United States Patent [19]

Yamahara et al.

[11] 4,082,767
[45] Apr. 4, 1978

[54] PRODUCTION OF ALPHA-AMINO ACIDS

[75] Inventors: Takeshi Yamahara, Itami; Shun Inokuma, Takatsuki, both of Japan

[73] Assignee: Sumitomo Chemical Company, Limited, Osaka, Japan

[21] Appl. No.: 671,984

[22] Filed: Mar. 30, 1976

[30] Foreign Application Priority Data

Apr. 3, 1975 Japan .................................. 50-41010

[51] Int. Cl.² .................. C07C 99/08; C07C 121/43; C07D 209/20
[52] U.S. Cl. .................. 260/326.14 T; 260/465.4; 260/514 J; 260/518 R; 260/519; 260/534 R; 260/534 C; 260/534 E; 260/534 G; 260/534 L; 260/534 M; 260/534 S
[58] Field of Search .................. 260/326.14 T, 518 R, 260/534 R, 534 S, 534 C, 534 E, 534 G, 534 M, 465.4, 514 J

[56] References Cited

U.S. PATENT DOCUMENTS

| 2,557,920 | 6/1951 | White | 260/534 R |
| 3,636,098 | 1/1972 | Shima et al. | 260/534 R |
| 3,790,599 | 2/1974 | Zundel | 260/326.14 T |

*Primary Examiner*—Dolph H. Torrence
*Attorney, Agent, or Firm*—Wenderoth, Lind & Ponack

[57] ABSTRACT

α-Amino acids are prepared by catalytically hydrolyzing a hydantoin compound of the formula,

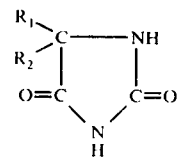

wherein $R_1$ and $R_2$ are individually hydrogen or an unsubstituted or substituted alkyl, cycloalkyl, alkenyl, aryl or aralkyl group, in the presence of imidazole or a derivative thereof.

9 Claims, No Drawings

PRODUCTION OF ALPHA-AMINO ACIDS

The present invention relates to a process for the production of α-amino acids.

α-Amino acids are useful for foodstuffs, feeds and medicines and also useful as intermediates for production of agricultural chemicals, medicines and high molecular compounds. It is known to hydrolyze a hydantoin compound to cleave the hydantoin nucleus, whereby a corresponding α-amino acid is obtained, and a large number of the hydrolysis processes have heretofore been proposed. For example, a process comprising hydrolyzing a hydantoin in the presence of an alkali metal compound (i.e. sodium hydroxide) or an alkaline earth metal compound is known, with such drawbacks that at least equimolar amount of the alkali metal or alkaline earth metal is required to conduct the hydrolysis effectively, and a large amount of an acid (i.e. sulfuric acid) is required to isolate the resulting α-amino acid. Moreover, in a purification step, i.e. crystallization step applied for the above-said process to eliminate the alkali metal salts which contaminated the α-amino acids, the purification yield is not always satisfactory.

The present inventors have studied to improve the process for production of α-amino acids by hydrolyzing a hydantoin compound, and found that the hydantoin compound is catalytically hydrolyzed in the presence of an imidazole compound as a catalyst, whereby α-amino acids are readily obtained at low costs, whereas the formation of by-products is effectively prevented.

The present invention provides a novel process for production of α-amino acids, which comprises catalytically hydrolyzing a hydantoin compound of the formula (I),

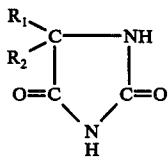

wherein $R_1$ and $R_2$ are individually a hydrogen atom or an alkyl, cycloalkyl, alkenyl, aralkyl or aryl group.

In the above definition, the term "alkyl" is intended to mean a straight or branched $C_1 - C_6$ alkyl which may be unsubstituted or substituted by a $C_1 - C_2$ alkoxy, hydroxyl, $C_1 - C_2$ alkylthio, mercapto, carbonyl, carboxyl, amino, cyano or indolyl group. The term "cycloalkyl" is intended to mean a $C_5 - C_7$ cycloalkyl which may be unsubstituted or substituted by a $C_1 - C_2$ alkoxy, hydroxyl, carbonyl or $C_1 - C_2$ alkylthio group. The "alkenyl" is a $C_2 - C_6$ alkenyl having one double bond in the molecule, which may be unsubstituted or substituted by a $C_1 - C_2$ alkoxy, hydroxyl or carbonyl group. The "aralkyl" is a $C_7 - C_9$ aralkyl which may be unsubstituted or substituted by a $C_1 - C_2$ alkoxy, hydroxyl, $C_1 - C_2$ alkylthio or mercapto group. The "aryl" is a $C_6 - C_8$ aryl which may be unsubstituted or substituted by a $C_1 - C_2$ alkoxy, hydroxyl, $C_1 - C_2$ alkylthio or mercapto group.

The imidazole compound used in the present invention includes a compound of the formula (II), or a compound having the formula (II) in its molecule,

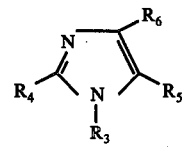

wherein $R_3$ is a hydrogen atom or an alkyl, alkenyl, aralkyl or aryl group, and $R_4$, $R_5$ and $R_6$ are individually a hydrogen or halogen atom or an alkyl, alkenyl, aralkyl or aryl group.

In the above definition, the term "alkyl" is intended to mean a $C_1 - C_5$ alkyl which may be unsubstituted or substituted by a carboxyl, amino, mercapto or hydroxyl group; the term "alkenyl" is a $C_2 - C_5$ alkenyl wherein a $C_2 - C_5$ alkenyl, i.e. vinyl group, includes its polymer, which alkenyl may be unsubstituted or substituted by an amino, carboxyl, mercapto or hydroxyl group; the "aralkyl" is a $C_7 - C_9$ aralkyl which may be unsubstituted or substituted by an amino, carboxyl, mercapto or hydroxyl group; and the "aryl" is a $C_6 - C_8$ aryl which may be unsubstituted or substituted by an amino, carboxyl, mercapto or hydroxyl group.

Examples of the imidazole compound include imidazole, N-methylimidazole, 2,4,5-triphenylimidazole, histamine, 3-methylimidazole, iodoimidazole, benzimidazole, 2-phenylbenzimidazole, dimethylimidazole, N-ethylimidazole or 3-ethylimidazole, or a homopolymer of N-vinylimidazole, 5-vinylimidazole or polyvinylimidazole, a copolymer of vinylimidazole and acrylic ester, a copolymer of vinylimidazole, acrylic ester and vinyl acetate, a copolymer of vinylimidazole and divinylbenzene, or a high molecular weight compound prepared by reacting a copolymer of 4-vinylpyridine and divinylbenzene with 2,4-dinitro-chlorobenzene and further reacting the resultant compound with an amine such as histamine to introduce a substituent such as imidazole group to the pyridyl group. The imidazole compound can be used as it is, or in an insoluble form prepared by a physical adsorption on or a chemical bond with silica gel or the like.

Examples of the hydantoin (I) used in the present invention include hydantoin, 5-methyl-hydantoin, 5-ethylhydantoin, 5-propylhydantoin, 5-isopropylhydantoin, 5-butylhydantoin, 5-phenylhydantoin, 5-cyclohexylhydantoin, 5-carboxymethylhydantoin, 5-aminomethylhydantoin, 5-methoxymethylhydantoin, 5-mercaptomethylhydantoin, 5-hydroxymethylhydantoin, 5-(β-carboxyethyl)hydantoin, 5-(β-methylthioethyl)hydantoin, 5-(α-hydroxyethyl)hydantoin, 5-(β-aminoethyl)hydantoin, 5-(β-cyanoethyl)hydantoin, 5-benzylhydantoin, 5,5-dimethylhydantoin, 5,5-methylethylhydantoin, 5,5-ethylpropylhydantoin or 5-indolylmethylhydantoin.

In carrying out the process of the present invention, a mixture of the hydantoin (I) and the imidazole (II) as the catalyst is heated in an aqueous medium. The reaction temperature is from room temperature (about 20° C.) to about 250° C., favorably from about 100° to about 200° C. The reaction velocity increases with raising the reaction temperature, but too high temperature unfavorably promotes a side-reaction. The mixing ratio by weight of the hydantoin (I) to water in the aqueous medium may optionally be varied depending on the reaction conditions, and is usually about 1:100 to 50:100. The aqueous medium may contain an inert solvent such as dimethylsulfoxide, N,N-dimethylformamide and 1,4-dioxane. The reaction time is not critical to the reaction of the present invention, but it is usually 0.5 to 10 hours. The imidazole (II) is used in a catalytically effective amount variable depending on the type of reaction, i.e. continuous reaction or batchwise reaction, and is usually used in an amount of at least 0.1 mol % on the basis of the hydantoin (I), from 1 to 50 mol % yielding favorable results and up to 1000 mol % providing commercially satisfactory results. The reaction velocity is increased with increase of the imidazole (I) used.

The reaction pressure is not limited, but in a high temperature reaction, the pressure increases due to the vapor pressure of water and ammonia and carbon dioxide gas generated during the reaction. It is markedly effective for increasing the production yield of α-amino acids to eliminate the generated gases out of the reaction system.

The present invention will be explained in more detail with reference to the following Examples, which are only illustrative but not limitative of the present invention.

EXAMPLE 1

A mixture of 1.74 g. of 5-(β-methylthioethyl)hydantoin, 68 mg. of imidazole and 20 ml. of water was heated to 160° C. in a 50 ml. autoclave and then allowed to react for 3 hours at 160° C., while being stirred. After the reaction was over, the autoclave was rapidly cooled to room temperature and the residual pressure was released. The autoclave was given a good wash with water to take off the reaction mixture, and then the reaction mixture was subjected to evaporation to dryness by means of a rotary evaporator. The resulting solid was shaken sufficiently with 100 ml. of methyl acetate. The methyl acetate insoluble matter was separated from the methylacetate solution. A portion of of the insoluble matter was recrystallized from water and then subjected to an infrared absorption spectrum and melting point measurements (m.p. 267° C., decomposed). Thus, it was found to be methionine. On the other hand, the methyl acetate soluble matter was found to be unreacted 5-(β-methylthioethyl)hydantoin and a negligible amount of by-products. According to a copper chelatemetric colorimetry of the insoluble matter (the colorimetry was conducted according to the method described in the specification of Japanese Laid-Open Patent Application No. 116008/1974), it was found that 0.75 g. of methionine (yield 50%) was attained.

The yield of α-amino acid above and in Examples and the following Comparative Examples is calculated by the following equation.

Yield of the produced amino acid $$= \frac{\text{Mol number of the produced amino acid}}{\text{Mol number of the hydantoin feed}} \times 100$$

COMPARATIVE EXAMPLE 1

Example 1 was repeated, provided that the catalyst, imidazole, was not used, and then only 0.24 g. of methionine was obtained as the methyl acetate insoluble matter (yield 17%).

EXAMPLES 2 TO 6 AND COMPARATIVE EXAMPLES 2 TO 6

According to a manner similar to that of Example 1, the hydrolysis of the hydantoin compounds shown in Table 1 was conducted at 160° C. for 3 hours in the presence of imidazole compounds in an amount shown in Table 1, and each corresponding α-amino acid was obtained. The results were as shown in Table 1 (Examples 2 to 6).

Examples 2 to 6 were repeated except that each imidazole compound was not used. The results were as shown in Table 1 (Comparative Examples 2 to 6).

Table 1

| | No. | Hydantoin | Amount (g) | Amount of imidazole (mg) | Amount of water (ml) | α-Amino acid | Amount obtained (g.) | Yield (%) |
|---|---|---|---|---|---|---|---|---|
| Example | 2 | Hydantoin | 1.0 | 68 | 20 | Glycine | 0.45 | 60 |
| | 3 | 5-Methyl-hydantoin | 1.14 | 68 | 20 | Alanine | 0.36 | 40 |
| | 4 | 5-isopropyl-hydantoin | 1.42 | 68 | 20 | Valine | 0.67 | 40 |
| | 5 | 5-Benzyl-hydantoin | 1.90 | 68 | 20 | Phenylalamine | 0.83 | 50 |
| | 6 | 5,5-Dimethyl-hydantoin | 1.25 | 68 | 20 | α,α-Dimethyl-glycine | 0.30 | 30 |
| Comparative Example | 2 | Hydantoin | 1.0 | 0 | 20 | Glycine | 0.19 | 25 |
| | 3 | 5-Methyl-hydantoin | 1.14 | 0 | 20 | Alanine | 0.19 | 21 |
| | 4 | 5-Isopropyl-hydantoin | 1.42 | 0 | 20 | Valine | 0.15 | 13 |
| | 5 | 5-Benzyl-hydantoin | 1.90 | 0 | 20 | Phenylalanine | 0.44 | 27 |
| | 6 | 5,5-Dimethyl-hydantoin | 1.25 | 0 | 20 | α,α-Dimethyl-glycine | 0.10 | 10 |

EXAMPLE 7

A mixture of 1.74 g. of 5-(β-methylthioethyl)hydantoin, 68 mg. of imidazole and 20 ml. of water was heated to 160° C. in a 50 ml. autoclave, and was allowed to react at 160° C. for 6 hours. After the reaction was over, the autoclave was rapidly cooled. The reaction mixture was treated by the same after-treatment as in Example 1 and methionine was obtained in yield of 80%.

EXAMPLE 8

Example 7 was repeated, except that the reaction was conducted at 180° C. for 3 hours, and methionine was obtained in yield of 91%.

EXAMPLE 9

Example 7 was repeated, except that the reaction was conducted at 160° C. for 3 hours using 82 mg. of N- methylimidazole in place of 68 mg. of imidazole, and methionine was obtained in yield of 60%.

What is claimed is:

1. A process for preparing an α-amino acid, which comprises catalytically hydrolyzing a hydantoin compound of the formula (I)

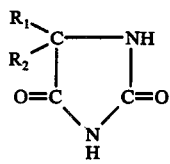

wherein $R_1$ and $R_2$ are individually selected from the group consisting of (1) hydrogen, (2) $C_1 - C_6$ alkyl which may be unsubstituted or substituted by $C_1 - C_2$ alkoxy, hydroxyl, $C_1 - C_2$ alkylthio, mercapto, carbonyl, carboxyl, amino, cyano or indolyl, (3) $C_5 - C_7$ cycloalkyl which may be unsubstituted or substituted by $C_1 - C_2$ alkoxy, hydroxyl, carbonyl or $C_1 - C_2$ alkylthio, (4) $C_2 - C_6$ alkenyl, having one double bond in the molecule, which may be unsubstituted or substituted by $C_1 - C_2$ alkoxy, hydroxyl or carbonyl, (5) $C_7 - C_9$ aralkyl which may be unsubstituted or substituted by $C_1 - C_2$ alkoxy, hydroxyl, $C_1 - C_2$ alkylthio or mercapto, and (6) $C_6 - C_8$ aryl which may be unsubstituted or substituted by $C_1 - C_2$ alkoxy, hydroxyl, $C_1 - C_2$ alkylthio or mercapto, in admixture with, as catalyst, (A) an imidazole compound of the formula (II)

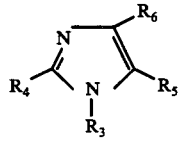

wherein $R_3$ is selected from the group consisting of (1) hydroge, (2) $C_1 - C_5$ alkyl which may be unsubstituted or substituted by carboxyl, amino, mercapto or hydroxyl, (3) $C_2 - C_5$ alkenyl which may be unsubstituted or substituted by amino, carboxyl, mercapto or hydroxyl, (4) $C_7 - C_9$ aralkyl which may be unsubstituted or substituted by amino, carboxyl, mercapto or hydroxyl, and (5) $C_6 - C_8$ aryl which may be unsubstituted or substituted by amino, carboxyl, mercapto or hydroxyl, and $R_4$, $R_5$ and $R_6$ are individually selected from the group consisting of halogen and the groups set forth above with respect to the definition of $R_3$, or (B) a compound containing the formula (II) in its molecule selected from the group consisting of a homopolymer of N-vinylimidazole, a homopolymer of 5-vinylimidazole, a homopolymer of polyvinylimidazole, a copolymer of vinylimidazole and an acrylic ester, a copolymer of vinylimidazole, an acrylic ester and vinyl acetate, a copolymer of vinylimidazole and divinylbenzene, and a compound prepared by reacting a copolymer of 4-vinylpyridine and divinylbenzene with 2,4-dinitro-chlorobenzene and further reacting the resultant compound with an amine.

2. The process according to claim 1, wherein the hydantoin compound is hydantoin, 5-methylhydantoin, 5-ethylhydantoin, 5-propylhydantoin, 5-isopropylhydantoin, 5-butylhydantoin, 5-phenylhydantoin, 5-cyclohexylhydantoin, 5-carboxymethylhydantoin, 5-aminomethylhydantoin, 5-methoxymethylhydantoin, 5-mercaptomethylhydantoin, 5-hydroxymethylhydantoin, 5-(β-carboxyethyl)hydantoin, 5-(β-methylthioethyl)hydantoin, 5-(α-hydroxyethyl)hydantoin, 5-(β-aminoethyl)hydantoin, 5-(β-cyanoethyl)hydantoin, 5-benzylhydantoin, 5,5-dimethylhydantoin, 5,5-methylethylhydantoin, 5,5-ethylpropylhydantoin, or 5-indolylmethylhydantoin.

3. The process according to claim 1, wherein the hydrolysis is conducted in an aqueous medium.

4. The process according to claim 3, wherein the aqueous medium is water.

5. The process according to claim 4, wherein the weight ratio of the hydantoin compound to water is about 1:100 to 50:100.

6. The process according to claim 1, wherein the hydrolysis is conducted at a temperature of room temperature to 250° C.

7. The process according to claim 1, wherein the catalyst is used in a catalytic amount.

8. The process according to claim 7, wherein the catalytic amount is at least 0.1 mol % on the basis of the hydantoin compound.

9. The process according to claim 1, wherein the catalyst is imidazole, N-methylimidazole, 2,4,5-triphenylimidazole, histamine, 3-methylimidazole, iodoimidazole, benzimidazole, 2-phenylbenzimidazole, dimethylimidazole, N-ethylimidazole, 3-ethylimidazole, a homopolymer of N-vinylimidazole, a homopolymer of 5-vinylimidazole, a homopolymer of polyvinylimidazole, a copolymer of vinylimidazole and an acrylic ester, a copolymer of vinylimidazole, an acrylic ester and vinyl acetate, a copolymer of vinylimidazole and divinylbenzene, or a compound prepared by reacting a copolymer of 4-vinylpyridine and divinylbenzene with 2,4-dinitro-chlorobenzene and further reacting the resultant compound with an amine.

* * * * *